United States Patent [19]

Siprut

[11] Patent Number: 6,009,555
[45] Date of Patent: Jan. 4, 2000

[54] MULTIPLE COMPONENT HEADGEAR SYSTEM

[76] Inventor: Leonard Albert Siprut, 4822 Santa Monica Ave., No. 265, San Diego, Calif. 92107

[21] Appl. No.: 08/882,051

[22] Filed: Jun. 25, 1997

[51] Int. Cl.$^7$ ....................................................... A61F 9/00
[52] U.S. Cl. ........................... 2/12; 2/15; 2/171; 2/209.3; 2/DIG. 11
[58] Field of Search ............................ 2/10, 12, 15, 171, 2/DIG. 11, 195.1, 209.13, 209.3, 209.4, 13

[56] References Cited

U.S. PATENT DOCUMENTS

| | | | |
|---|---|---|---|
| 566,326 | 8/1896 | Kirshner | 2/10 |
| 2,004,471 | 6/1935 | David | 2/10 |
| 4,192,017 | 3/1980 | Fay . | |
| 4,547,903 | 10/1985 | Brown et al. . | |
| 4,768,231 | 9/1988 | Schrack . | |
| 4,951,316 | 8/1990 | Moody . | |
| 5,105,475 | 4/1992 | Lynd et al. . | |

OTHER PUBLICATIONS

SunSense, Inc., "Visor and Sunglasses," Copyright 1996, pp. 1–2, Brochure.

*Primary Examiner*—Diana Oleksa
*Attorney, Agent, or Firm*—Presseisen & Reidelbach, P.C.; Charles F. Reidelbach, Jr.

[57] ABSTRACT

The present invention incorporates a unique system of attaching multiple headgear components upon the user so as to increase the overall effectiveness of the headgear during extreme sporting conditions. This is accomplished by providing a headgear apparatus having a visor member which is removably secured to and independently adjustable from a headband member. The visor member surface is uniquely designed with a lightwave transmissive gradient. An eye shield member is removably secured to the headband member by the same set of rivets and is adjustable to provide a desired distance between the eye shield member and the user's eyes. A sealant material is selectively placed between the headband member and the user's forehead so as to prevent water from interfering with the eyes and face of the user during use as well as provide a stabilizing grip. A protective hood member and mask may be removably secured by a set of rivets to the headband member and is securely fitted upon the head of the user by a chin strap. Finally, a cord member is removably fastened by a set of rivets to both the headband member and a piece of wearing apparel, and is adjustable in length by an adjustment buckle to obtain a desired tension when in use.

9 Claims, 3 Drawing Sheets

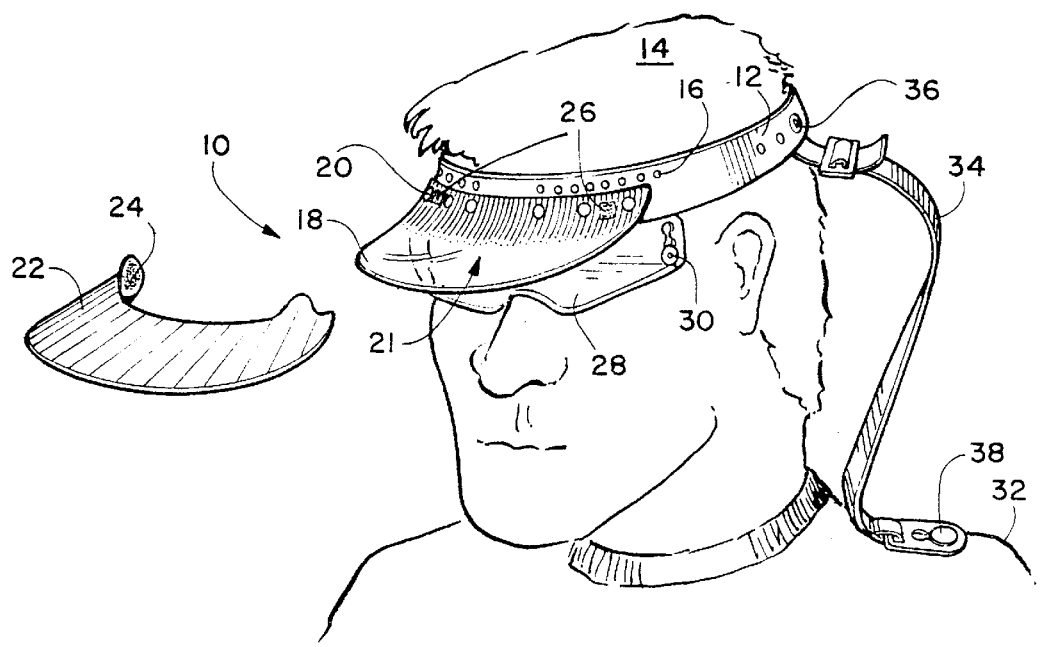
FIGURE 1
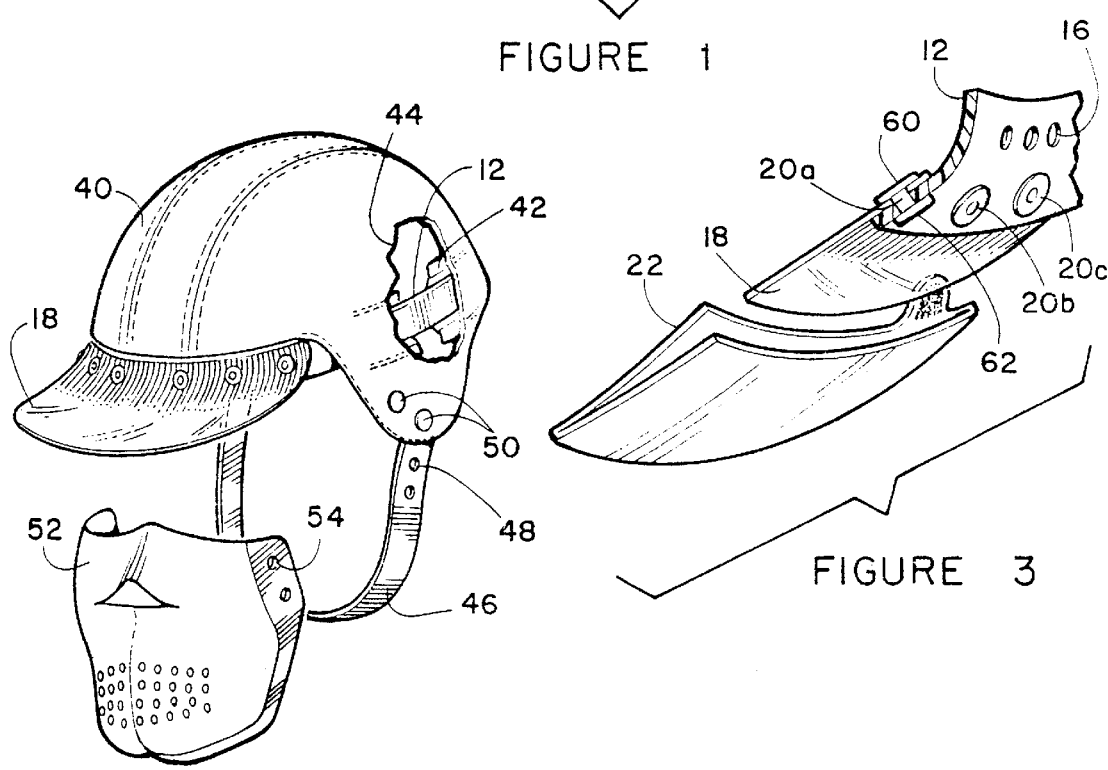
FIGURE 2
FIGURE 3

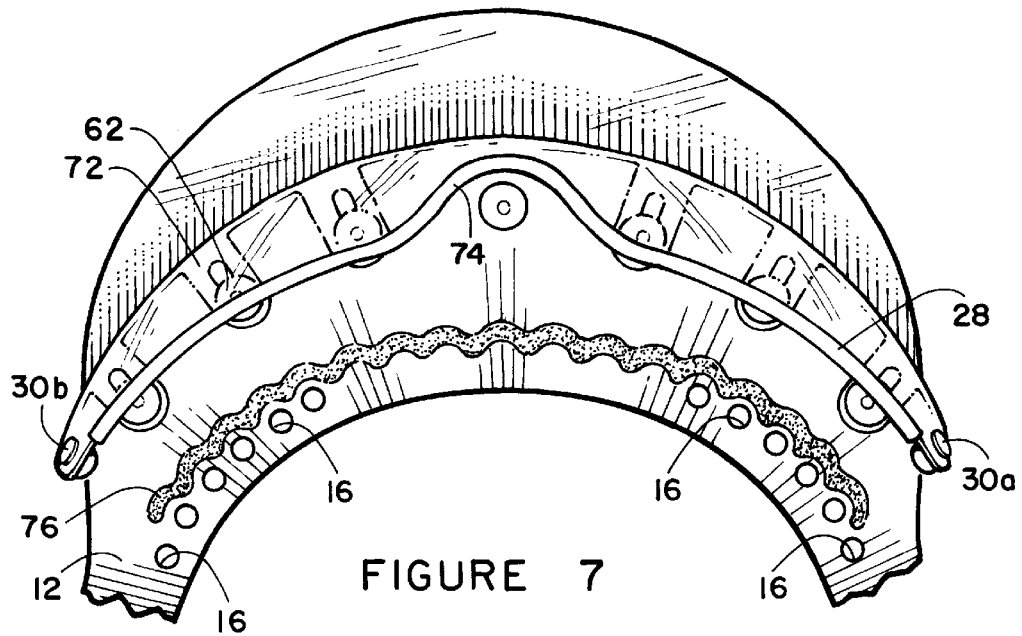
FIGURE 7
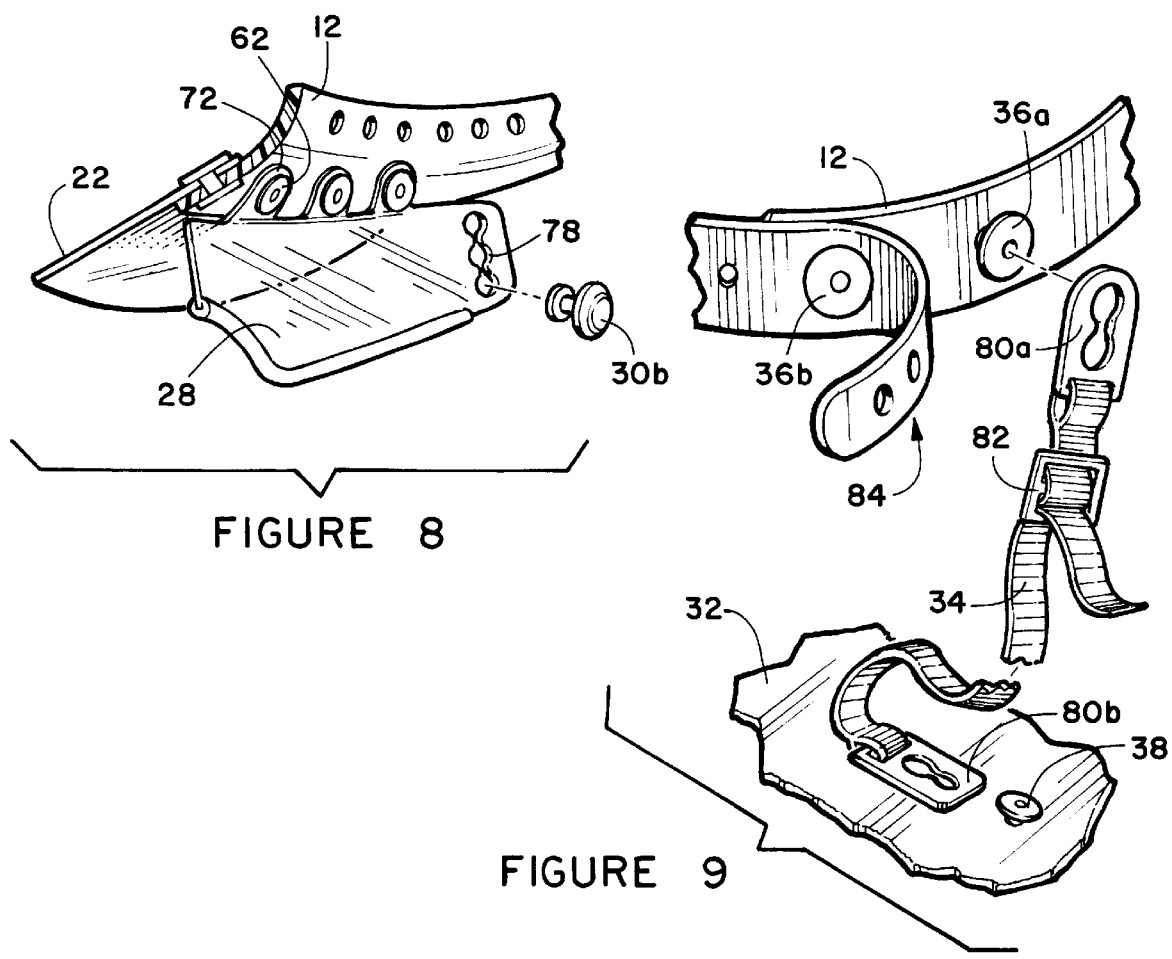
FIGURE 8
FIGURE 9

MULTIPLE COMPONENT HEADGEAR SYSTEM

FIELD OF THE INVENTION

The present invention pertains generally to headgear devices and systems, and more particularly to headgear adaptable for use in a variety of high activity sporting conditions. The present invention enhances pre-existing concepts in headgear technology by incorporating a unique system of attaching and adjusting multiple headgear components upon the user so as to increase the overall effectiveness of the headgear during extreme sporting conditions.

BACKGROUND OF THE INVENTION

There is a variety of headgear devices which are commonly and widely utilized for protecting a person's face from the sun, wind or particulate matter during high action sporting activities such as surfing, water skiing, snow skiing, snowmobiling and the like. These devices typically combine a fixed visor type structure worn on the head of the user with a connectable eye shield that can be rotated either up or down or positioned at variable distances from the wearer's eyes. Examples of these kinds of devices are disclosed in U.S. Pat. No. 4,951,316, issuing to Moody, U.S. Pat. No. 4,768,231, issuing to Schrack, and U.S. Pat. No. 5,105,475, issuing to Lynd et. al.

While these devices may be suitable under some sporting conditions, they are ineffective in many high-action sporting activities, especially those involving extreme conditions such as surfing, skiing, etc. Another problem with these prior art headgear devices is that they are unable to provide the necessary flexibility and adaptability often required by the sports enthusiast who engages in a wide variety of different sporting activities.

For instance, in many extreme sporting conditions, such as surfing, a condition is presented in which the sun or the glare therefrom as reflected on the ocean presents a visual impediment. It is particularly bothersome for surfers since their body position on the surfboard frequently changes. Consequently, there is a need for device which allows independent lateral adjustment of the visor to a further extended or contracted position. The condition is also presented in which the glare on the ocean is immediately presented yet the user is unable to respond by physically re-adjusting the positioning of the visor or eye shield upon the head. The reason for this is that the user may not have any hands available to perform this function or the event takes place too rapidly. This loss in vision both inhibits performance of the sport, increases the risk of a mishap, and increases the damage which the sun's glare causes upon the eyes over prolonged periods.

Aside from their ineffectiveness, prior art headgear devices lack the necessary flexibility and adaptability to different sporting conditions. For example, some sporting conditions require more headgear protection while other conditions require less. However, the attachment or removal of various headgear components is often not an option as it is either difficult and time consuming or interferes with the operation and performance of the device.

For example, it is also the case where a protective waterproof hood is necessary and desirable to prevent ear infection or reduce the loss of body heat. However, as with most prior art devices, the attachment or addition of the hood would typically interfere with the functionality of the headgear device not allowing for the proper adjustment of the eye shield, etc.

Another feature which appears to be missing in prior art devices is the connectability of the device to the user in cases where the entire headgear device is dislocated and/or dislodged. Although some devices teach buoyancy, such as that taught by Schrack, obtaining the located device is quite another story.

Accordingly, there is a need for increasing the flexibility and adaptability of headgear for use in a wide variety of different sporting activities. Additionally, there is a need for providing a more effective headgear device for use in high-action sporting activities, especially those involving extreme conditions.

SUMMARY OF THE INVENTION

It is the object of the present invention to provide an improved headgear device which is both flexible and adaptable for use in a variety of different sporting environments, including water, wind, snow, and the like.

It is another object of the present invention to provide an improved headgear device which provides improved effectiveness in high-action sporting activities such as surfing, water skiing, snow skiing, snowmobiling and the like.

It is yet another object of the present invention to provide an improved headgear device which allows "hands-free" relief of sun glare without obstruction of vision by a simple slight turning or tilting of the user's head.

It is another object of the present invention to provide an improved headgear device which allows independent and localized area adjustment of the visor without physically disturbing the attachment mechanism of the headgear upon the user's head.

It is another object of the present invention to provide an improved headgear device which allows rapid and easy attachment and removal of various components of the headgear system such as a visor, eye shield, protective hood, connecting cord, etc.

It is another object of the present invention to provide an improved headgear device which allows for connectability to the user's wearing apparel to prevent loss of the headgear during extreme activities.

It is another object of the present invention to provide a visor which utilizes a cord to assist in the proper positioning of the visor upon the head of the user.

Finally, it is an object of the present invention to provide the above-mentioned improvements yet is simple and inexpensive to manufacture.

These and other objects are achieved in accordance with the present invention by providing a headgear apparatus having a main body or headband member which is fitted and worn upon a user's head. The headband member, formed of neoprene fabric, has a frontal portion which is placed proximate the user's forehead and substantially extends across the forehead to form a crescent-shaped surface. An independently adjustable visor member, also exhibiting a crescent-shaped surface, is removably secured to the frontal portion of the headband member by a set of rivets. An increased lightwave transmissive characteristic is exhibited as the surface of the visor member extends radially from the visor member's innermost or concave edge to its outermost or convex edge. A mesh or opaque visor cover may be provided for increased lightwave protection as desired.

The same set of rivets which removably secure the visor member to the headband member also removably secure the eye shield member. The eye shield member is configured as desired to extend across a portion of the user's face in frontal blocking relationship to the user's eyes. The distance between the eye shield member and the user's eyes may be adjustable in accordance with the preferred embodiment. The present invention features a water sealant material which is strategically and selectively placed on the headband member so as to prevent water interference or disturbance with the eyes and face of the user while also increasing the stability or grip of the headband on the forehead of the user.

In furtherance of the objectives of the present invention, a protective hood member may also be removably secured by a set of rivets to the headband member and is secured fastened upon the head of the user by an adjustable chin strap. As desired, a breathable mask member may be removably secured to the protective hood member for added facial protection.

Finally, the present invention features a cord member which extends between a first and second end and is removably secured to the headband member and piece or pieces of wearing apparel by one or more rivets. The cord is adjustable in length by an adjustment buckle located therein.

Further detail regarding the headgear apparatus and system in accordance with the present invention may be had with reference to the detailed description which is provided below, taken in conjunction with the following illustrations.

BRIEF DESCRIPTION OF THE DRAWINGS

FIG. 1 is an overall perspective view of the present invention with an exploded view of the visor cover;

FIG. 2 is a perspective view of the alternative attachments to the present invention with a portion of the protective hood member cut-away to illustrate the internal headband connecting loops;

FIG. 3 is an exploded view of a portion of the present invention showing a cross-sectional perspective view of the visor member attachment to the headband member;

FIG. 7 is a bottom view of the present invention showing the attachment of the eye shield member to the headband member as well as the location and placement of sealant material upon the surface of the headband member;

FIG. 8 is an exploded view of a portion of the present invention showing a cross-sectional perspective view of the visor member and eye shield member attachment to the headband member; and FIG. 9 is a perspective view illustrating the cord and its interconnection to the user's wearing apparel and headband member, as well as illustrating the adjustability in size of the headband member itself.

DETAILED DESCRIPTION OF THE PREFERRED EMBODIMENT

Figure 4:
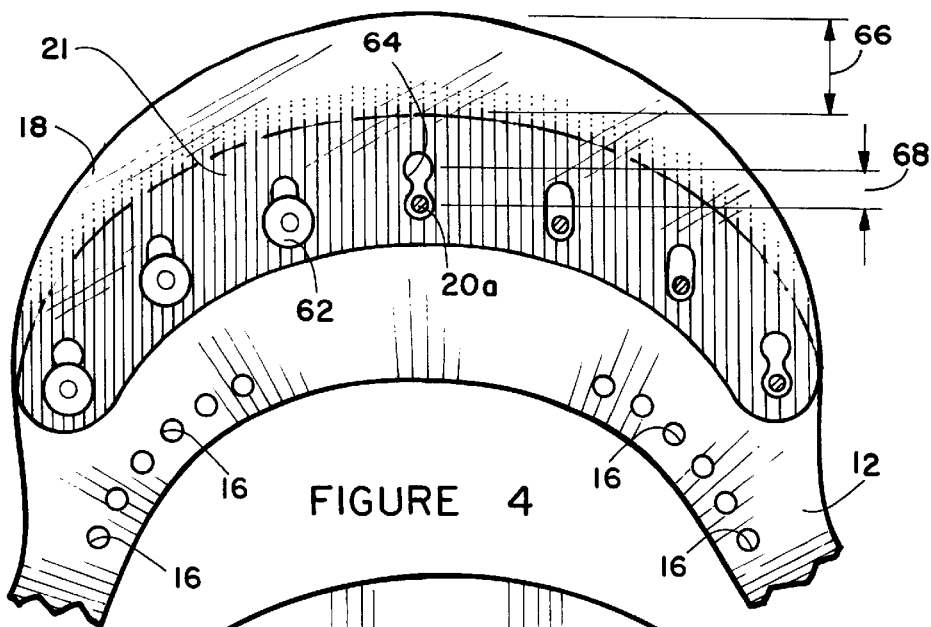
FIG. 4 is a plan view of the headgear apparatus showing the adjustability and movability between the headband member and visor member.

The general environment of the preferred embodiment of the present invention is shown and illustrated in FIG. 1. A headgear assembly 10 comprises a headband member 12 fitted around the head 14 of a user. The headband member 12 is preferably made from a flexible material which is both water and weather resilient and is not likely to be adversely affected by salt water, perspiration, cold or hot temperatures, or other extreme elements. Although other materials may be used, extensive research and development has determined that a headband member 12 made from a single piece of neoprene fabric, similar to that used in the manufacture of wet suits, both satisfies the above objectives while also providing desirable floatation characteristics.

The widest area of the headband member 12 is the frontal portion which, when worn, conforms to the area of the user's forehead directly above the user's eyebrows. The frontal portion of the headband member 12 has a crescent-shaped surface with an upper concave-shaped edge and a lower convex-shaped edge. As shown in FIG. 1, the headband member 12 has a series of ventilation holes 16 uniformly spaced in a longitudinal relationship proximate the concave-shaped edge of the frontal portion of the headband member 12. It is to be noted that the present invention contemplates a number of ventilation hole patterns and positions.

A visor member 18, also having a crescent-shaped surface with concave and convex-shaped edges, is positioned adjacent and extends across the convex-shaped frontal portion of the headband 12. The surface of the visor member 18 exhibits a lightwave transmissive gradient 21 from opaque at the convex-shaped edge to slightly shaded or tinted at the concave-shaped edge. Additionally, the visor member 18 may provide ultraviolet protection as desired to screen out the undesirable sun rays.

The visor member 18 is preferably secured to the headband 12 by way of multiple rivets 20 which are uniformly spaced in a longitudinal relationship across the frontal portion of the headband member 12. The present invention contemplates the use of other well known securing devices such as hook and loop fasteners. The visor member 18 may be easily attached and removed from the headband member 12 to allow interchangeability of visor members having different sizes, shapes and styles.

Figure 5:
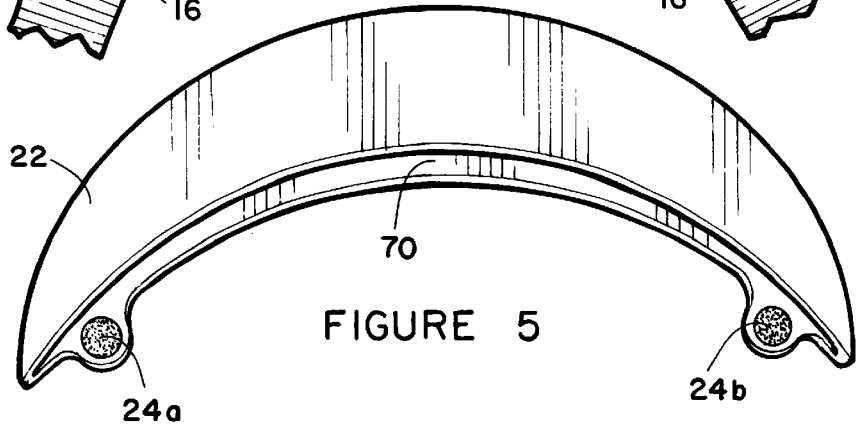
FIG. 5 is a plan view of the visor cover.

As desired, a mesh or opaque visor cover 22 may be placed around the visor 18 and fastened thereto by any means well known in the art such as hook and loop portions 24, 26, respectively. The exploded view of FIG. 5 shows the visor cover 22 having a pocket-like opening 70 for slidable engagement with visor member 18. The visor cover 22 may be securely fastened in place by adjacent positioning of loop portions 24a,b with their respective counterpart portions 26 on visor member 18. The present invention contemplates a variety of covers having different sizes, shapes, and lightwave transmissive intensities.

An eye shield member 28 of a configuration extending across a portion of the user's face in frontal blocking relationship to the user's eyes is mounted to the underside of the frontal portion of headband 12 by way of multiple rivets 20. The eye shield 28 may be bilaterally stabilized against both sides of the user's head 14 by way of spacers 30.

Finally, the headband member 12 may be fitted to one or more pieces of the user's wearing apparel 32 by way of a connecting cord 34. Preferably, one end of the cord 34 is attached to headband member 12 by means of rivet 36 and the opposite end is attached to the user's wearing apparel 32 by means of rivet 38. The present invention anticipates the use of semi-permanent rivets which may be removed and which do not damage the wearing apparel 32 during application or removal.

Turning now to FIG. 2, the present invention is shown with a protective hood member 40 attached to headband member 12. The protective hood member 40 may serve the purposes of: 1) preventing body heat loss escaping from the top of the head while the user is in a cold or wet environment; 2) providing a protective covering around the user's ears to prevent damage to the ear caused by the environment which is commonly experienced by persons in action sports such as surfing; and 3) preventing direct sun and heat damage to the head while permitting breathability of the headgear. Additionally, the protective hood member 40 may be formed from the same material as the headband member 12, a gortex fabric, or any other material well known in the art.

The cutout 44 of FIG. 2 best illustrates the loops 42 by which the headband 12 is inserted and thereby secured to protective hood member 40. The loops 42 may be adjustable so as to allow the proper fit of the hood member 40 upon the head of the user. Additionally, hood 40 may be secured to the frontal portion of headband 12 by way of rivets 20. Alternatively, additional rivets (not shown) may be inserted through the headband member 12 proximate the upper concave-shaped edge for the purpose of fastening the protective hood member 40 to the frontal portion of the headband member 12.

Figure 6:
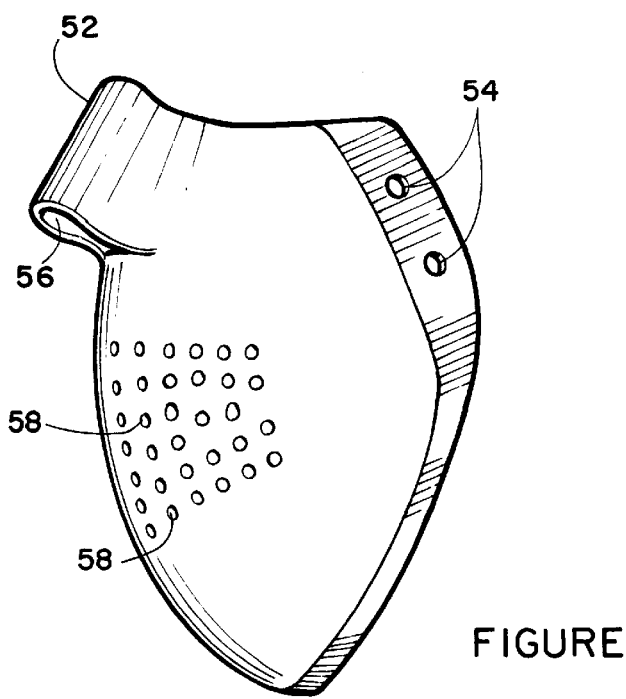
FIG. 6 is a side view of the protective mask member.

Finally, the protective hood member 40 and headband member 12 are secured to the head of the user by way of chin strap 46. More specifically, chin strap 46 is properly fitted to the user's head by selecting one of multiple circular cutouts 48 for attachment to one or more rivets 50 firmly secured to protective hood member 40. In addition, a protective mask member 52 is attachable to hood member 40 by fastening cutouts 54 onto rivets 50. As shown in FIG. 6, the mask member 52 features a nose portion 56 and mouth portion 58 which allows the user to breathe while still obtaining the protection desired.

FIG. 3 best illustrates the attachment of visor member 18 to headband member 12 by way of rivets 20*a–c*. More specifically, rivet 20*a* has a head portion 60 which is received by a shank portion 62 to form a secure attachment between visor member 18 and headband member 12.

The crescent-shaped surfaces of both the visor member 18 and the frontal portion of the headband member 12 is clearly illustrated in FIG. 4. More particularly, the visor member 18 extends beyond the headband member 12 a distance 66 as shown.

FIG. 4 also illustrates seven points of connection between the headband member 12 and visor member 18. Of the seven points of connection, three are slidably adjustable and four serve as guides for the movement of the visor member 18 to the adjustable positions. The connection points are comprised of a series of slots which are formed in the visor member 18, each for allowing the placement therethrough of the shank portions of rivets 20. As stated above, the slots are designed to allow adjustability and lateral movement of visor member 18 as it is secured to headband member 12. By way of example rather than limitation, the visor member 18 may be slidable a distance 68 of five sixteenths (5/16") of an inch.

More specifically, center slot 64 in FIG. 4 is uniquely shaped to provide either an extended or contracted position. Additionally, the unique shape of center slot 64 is repeated in the shapes of the outermost slots of visor member 18. The remaining slots merely provide guidance for the adjustment of the center and outermost connection points. This particular design allows independent and localized adjustment of one or more rivets within the center or outermost slots to provide a secure custom fit for the user.

During use, the user may adjust one or more of the connection points to allow for a more precise blocking of the sun's glare. For example, the user may adjust one the outermost connection points by extending that portion of the visor member 18 to a point where the sun avoids hitting his or her face. The adjustment can be made very rapidly with very little effort, making it very effective in high active sporting activities.

FIG. 4 also shows the upper surface of the visor member 18 as having a lightwave transmissive gradient 21 from opaque at the convex-shaped edge to slightly shaded at the concave-shaped edge. This gradient 21 allows for easy and momentary blocking of sun glare by the user by simply tilting his or her head in the opposite direction of the glare with no significant loss in visibility.

The attachment of eye shield member 28 to headband member 12 is best illustrated in FIGS. 7 and 8. More particularly, eye shield member 28 is suspended from headband member 12 by multiple tabs 72 which are slidably engaged with the shank portions of rivets 20 and removably secured between the ends 60, 62 of rivets 20. The eye shield member 28 may have a nose portion 74 which may rest or be placed above the nose of the user. A safety piece may be positioned along the arch of the nose portion 74 to prevent contact of the nose with the shield member 28. Preferably, eye shield member 28 is made of a material which is transmissive of lightwaves within the visible spectrum. In the preferred embodiment, the eye shield member 28 is made from a high impact plastic or shatter resistant glass having ultraviolet protection as desired. The eye shield member 28 may be easily detached with little effort, allowing for interchangeability of eye shields having different shapes, sizes, styles, and gradients.

As mentioned above, the eye shield member 28 preferably extends bilaterally to each temple of the user and is held in place or stabilized against the head of the user by way of bilateral spacers 30*a,b*. FIG. 8 illustrates multiple slots 78 for positioning spacers 30*a,b* as desired.

In accordance with the present invention, a series of ventilation holes 16 are uniformly spaced in a longitudinal relationship along the concave-shaped edge of the frontal portion of the headband member 12 is also shown in FIG. 7. These ventilation holes 16 are strategically placed mid-line over the front of the user's forehead to provide both aeration and breathability to the user's head as well as assisting with the rapid evaporation of perspiration which would otherwise drip into the user's eyes. The ventilation holes 16 serve the secondary purpose of providing an effective means for removing undesired water which would otherwise leak onto the user's face.

A sealant strip 76 exhibiting a continuous bead of siliconized rubber is placed on the underside of headband member 12 proximate the concave-shaped edge and between the ventilation holes 16 and rivets 20. In the preferred embodiment, the sealant strip 76 is a wavy longitudinal line running parallel to the line of ventilation holes 16 and extending around the head bilaterally to the ear line.

The purpose of the sealant strip 76 is to provide both a stabilizing grip to the user's forehead as well as prevent water from running under the frontal portion of the headband member 12 and across the user's eyes and face. During use, the sealant strip 76 either forces undesired water through the ventilation holes 16 or channels it across the headband member 12 to the area just above the user's ears. This unique feature is especially useful during the play of high activity water sports such as surfing.

Finally, referring to FIG. 9, the headband member 12 may be properly fitted about the head of the user by securing one of multiple holes 84 onto rivet 36*a* or 36*b*. This inherent adjustability in headband size allows the product to be manufactured relatively inexpensively.

Further, the headband member 12 may be fastened to the wearing apparel 32 of the user, such as shirts, shorts or wet suits, by way of a connecting cord 34. Preferably, one end of the cord 34 is attached to rivet 36*a* by way of connector 80*a*. Similarly, the opposite end of connecting cord 34 is attached to rivet 38 by way of connector 80*b*. As desired, an adjustment buckle 82 may be positioned therebetween so as to provide a proper fitted cord length. Additionally, cord 34 may be attached at a center rivet on the back of the visor (not shown) to allow for more consistent positioning of the headband member upon the head of the user.

It will therefore be understood that various changes in the details, materials and arrangement of parts which have been herein described and illustrated in order to explain the nature of the invention may be made by those skilled in the art within the principal and scope of the invention as expressed in the following claims.

I claim:

1. A headgear apparatus to be worn by a user comprising:
    a headband member for fitting about a user's head, said headband member having a frontal portion adapted to substantially extend across the forehead of a user;
    a visor member removably secured to said frontal portion of said headband, said visor member independently extendable from said headband; and
    an eye shield member removably secured to said frontal portion of said headband, said eye shield member being of a configuration adapted to extend across a portion of a user's face in frontal blocking relationship to a user's eyes.

2. A headgear apparatus as recited in claim 1, wherein said eye shield member is adjustable with respect to said headband member.

3. A headgear apparatus as recited in claim 1, wherein said visor member and said eye shield member are secured to said frontal portion of said headband member by a set of rivets.

4. A headgear apparatus as recited in claim 1, wherein said headband member is formed from neoprene fabric.

5. A headgear apparatus as recited in claim 1, wherein a continuous bead of sealant material is selectively placed on said headband member.

6. A headgear apparatus as recited in claim 1, wherein said visor member has a lightwave transmissive portion and an opaque portion.

7. A headgear apparatus as recited in claim 1, wherein said visor member has a crescent-shaped surface and a concave-shaped edge, and wherein said surface of said visor member is increasingly transmissive of lightwaves within the visible spectrum as said surface extends away from said concave-shaped edge.

8. A headgear apparatus as recited in claim 1, further comprising a visor cover for placement over said visor member.

9. A headgear apparatus as recited in claim 1, further comprising a cord for connecting said headband to a piece of wearing apparel of a user.

* * * * *